United States Patent
Vonakis et al.

(10) Patent No.: US 6,353,097 B1
(45) Date of Patent: Mar. 5, 2002

(54) NUCLEIC ACIDS ENCODING SIGNAL TRANSDUCTION INHIBITORS OF ALLERGIC REACTIONS

(75) Inventors: Becky M. Vonakis, Fairfax, VA (US); Henry Metzger, Chevy Chase; Huaxian Chen, Bethesda, both of MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/608,902

(22) Filed: Jul. 3, 2000

Related U.S. Application Data

(62) Division of application No. 09/020,116, filed on Feb. 6, 1997, now Pat. No. 6,084,063.

(51) Int. Cl.$^7$ .............................................. C07H 21/04
(52) U.S. Cl. ................... 536/23.5; 435/320.1; 435/325; 536/23.4
(58) Field of Search .............................. 536/23.1, 23.4, 536/23.5; 435/320.1, 325

(56) References Cited

PUBLICATIONS

Vonakis et al. "The Unique Domain as the Site on Lyn Kinase for Its Constitutive Association with the High Affinity Receptor for IgE", *J. Biol. Chem.* 272(38):24072–24080, Sep. 19, 1997.

Suzuki et al. "Early and Late Events in FcεRI Signal Transduction in Human Cultured Mast Cells", *J. Immunol.*, 159:5881–5888, 1997.

Bolen et al. "Leukocyte Protein Tyrosine Kinases: Potential Targets for Drug Discovery", *Annu. Rev. Immunol.*, 15:371–404, 1997.

Gauen et al. "Multiple Features of the p59$^{fyn}$ src Homology 4 Domain Define a Motif for Immune–Receptor Tyrosine–Based Activation Motif (ITAM) Binding and for Plasma Membrane Localization", *J. Cell. Biol.*, 133(5):1007–1015, Jun. 1996.

Lin et al. "The FcεR1βSubunit Functions as an Amplifier of FcεR1γ–Mediated Cell Activation Signals", *Cell* 85:985–995, Jun. 28, 1996.

Saouaf et al. "Reconstitution of the B Cell Antigen Receptor Signaling Components in COS Cells", *J. Biol. Chem.*, 270(45):27072–27078, Nov. 10, 1995.

Pleiman et al. "Distinct p53/56$^{lyn}$ and p59$^{fyn}$ Domains Associate with Nonphosphorylated and Phosphorylated Ig–α", *Proc. Natl. Acad. Sci. USA*, 91:4268–4272, May 1994.

Rider et al. "The cDNAs Encoding Two Forms of the LYN Protein Tyrosine Kinase are Expressed in Rat Mast Cells and Human Myeloid Cells", *Gene* 138:219–222, 1994.

Resh, Marilyn D. "Interactions of Tyrosine Kinase Oncoproteins with Cellular Membranes", *Biochimica et Biophysica Acta* 1155:307–322, 1993

Bolen et al. "The Src family of Tyrosine Protein Kinases in Hemopoietic Signal Transduction", *FASEB J.* 6:3403–3409, 1992.

Gauen et al. "p59$^{fyn}$ Tyrosine Kinase Associates with Multiple T–Cell Receptor Subunits Through its Unique Amino–Terminal Domain", *Mol. Cell. Biol.* 12(12):5438–5446, Dec. 1992.

Yamanashi et al. "The Yes–Related Cellular Gene Lyn Encodes a Possible Tyrosine Kinase Similar to p56$^{lck}$", *Mol. and Cellular Biol.*, 7(1):237–243, Jan. 1987.

Uckun et al. *J. Biol. Chem.* 271:6389–6397, 1996.

Pleiman et al. *Mol. Cell Biol.* 13:5877–5887, 1993.

*Primary Examiner*—Remy Yucel
*Assistant Examiner*—Bronwen M. Loeb
(74) *Attorney, Agent, or Firm*—Needle & Rosenberg, P.C.

(57) ABSTRACT

The present invention provides an isolated polypeptide consisting of amino acids 1–66 of the human tyrosine kinase, Lyn A, in a pharmaceutically acceptable carrier and an isolated polypeptide consisting of amino acids 1–45 of the human tyrosine kinase, Lyn B, in a pharmaceutically acceptable carrier. The present invention also provides isolated nucleic acids encoding the above-described amino acid sequences, as well as vectors comprising the nucleic acids and cells comprising the vectors. The present invention further provides a method of treating or preventing an allergic disorder in a subject, comprising administering any of the above nucleic acids to a cell of the subject under conditions whereby the nucleic acid is expressed in the subject's cells, thereby treating the allergic disorder. Additionally provided in this invention is a fusion protein comprising either a polypeptide consisting of amino acids 1–66 of the human tyrosine kinase, Lyn A or a polypeptide consisting of amino acids 1–45 of the human tyrosine kinase, Lyn B and a ligand which binds to and is internalized by cells which express a high affinity receptor for IgE on the surface. A method of treating or preventing an allergic disorder in a subject is also provided, comprising administering an effective amount of the above fusion protein to a cell of the subject, whereby the fusion protein treats the subject's allergic disorder.

18 Claims, 2 Drawing Sheets

SEQUENCE LISTING

```
<160> NUMBER OF SEQ ID NOS: 8

<210> SEQ ID NO 1
<211> LENGTH: 66
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 1

Met Gly Cys Ile Lys Ser Lys Gly Lys Asp Ser Leu Ser Asp Asp Gly
1               5                   10                  15

Val Asp Leu Lys Thr Gln Pro Val Arg Asn Thr Glu Arg Thr Ile Tyr
            20                  25                  30

Val Arg Asp Pro Thr Ser Asn Lys Gln Gln Arg Pro Val Pro Glu Ser
        35                  40                  45

Gln Leu Leu Pro Gly Gln Arg Phe Gln Thr Lys Asp Pro Glu Glu Gln
    50                  55                  60

Gly Asp
65

<210> SEQ ID NO 2
<211> LENGTH: 45
<212> TYPE: PRT
```

<213> ORGANISM: Artificial Sequence
<220> FEATURE:
<223> OTHER INFORMATION: Description of Artificial Sequence:/Note = synthetic construct

<400> SEQUENCE: 2

Met Gly Cys Ile Lys Ser Lys Gly Lys Asp Ser Leu Ser Asp Asp Gly
1               5                   10                  15

Val Asp Leu Lys Thr Gln Pro Val Pro Glu Ser Gln Leu Leu Pro Gly
            20                  25                  30

Gln Arg Phe Gln Thr Lys Asp Pro Glu Glu Gln Gly Asp
        35                  40                  45

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 3

Met Gly Cys Ile Lys Ser Lys Gly Lys Asp
1               5                   10

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 4

Met Gly Cys Ile Lys Ser Lys Gly Lys Asp Ser Leu Ser Asp Asp Gly
1               5                   10                  15

Val Asp Leu Lys Thr Gln Pro Val Arg Asn Thr
            20                  25

<210> SEQ ID NO 5
<211> LENGTH: 40
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 5

Thr Glu Arg Thr Ile Tyr Val Arg Asp Pro Thr Ser Asn Lys Gln Gln
1               5                   10                  15

Arg Pro Val Pro Glu Ser Gln Leu Leu Pro Gly Gln Arg Phe Gln Thr
            20                  25                  30

Lys Asp Pro Glu Glu Gln Gly Asp
        35                  40

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 6
cgggcggctc gatgggatgt attaaatcaa aaaggaaag                                 39

```
<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 7
cggcggctcg agctagtccc cttgctcctc tggatc                              36

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 8
gccaggcttg agggtcctta cagccacttt tgtgc                               35
```

US 6,353,097 B1

NUCLEIC ACIDS ENCODING SIGNAL TRANSDUCTION INHIBITORS OF ALLERGIC REACTIONS

This application is a divisional of, and claims the benefit of, application Ser. No. 09/020,116, filed Feb. 6, 1997, now U.S. Pat. No. 6,084,063, issued Jul. 4, 2000, which application is hereby incorporated in its entirety herein by reference.

BACKGROUND OF THE INVENTION

1. Field of the Invention

The present invention is directed to the prevention and treatment of an allergic disorder. In particular, the invention relates to the administration of polypeptides of the unique domain of the tyrosine kinase, Lyn, to the cells of a subject having, or at risk of having, an allergic disorder. The polypeptides act within the cells to bind the cytoplasmic domain of the high affinity receptor of IgE (FcεRI) and inhibit signaling through the receptor which would result in release of histamines and other substances associated with an allergic reaction, thereby preventing or treating an allergic disorder.

2. Background Art

The family of proteins known as the "multichain immune recognition receptors" includes the antigen receptors on B and T-lymphocytes and Fc receptors including the receptor with high affinity for IgE (FcεRI) (1). Highly homologous in structure, all these receptors utilize, at least in part, a common mechanism to initiate cellular responses: multivalent interactions with antigen leads to aggregation of the receptors and is followed by enhanced phosphorylation of tyrosines, in the Immune-Receptor Tyrosine-based Activation Motifs (ITAMs) within the cytoplasmic domains of the receptor itself, by a receptor-associated Src-family kinase (2).

Aggregation of the FcεRI on mast cells initiates a cascade of events leading to degranulation and release of mediators responsible for the symptoms of atopy. Among the earliest events in the FcεRI cascade is the phosphorylation of tyrosines in the ITAMs on the β and γ chains of the receptor by the Src-family kinase, Lyn.

Several groups have studied the interaction between FcεRI and Lyn kinase by a variety of techniques and have demonstrated (7–10) a direct interaction between the kinase and the C-terminal cytoplasmic extension of the receptor's β chain. Previous studies have also demonstrated that two forms of Lyn, designated Lyn A and Lyn B, are produced by differential mRNA splicing, both of which behave equivalently (5) and become equivalently attached to the receptor after chemical cross-linking (4).

For FcεRI, a "transphosphorylation" mechanism has been demonstrated that accounts for the earliest cascade events (3,4). Data from these earlier studies showed that a small percentage of resting (unphosphorylated) receptors are constitutively associated with Lyn and this constitutive association with the kinase is an absolute requirement for the initial phosphorylation of the receptor.

The present invention provides polypeptides comprising the unique region of the Lyn kinase which bind the C-terminal cytoplasmic domain of the β chain of the FcεRI and inhibit activation of the FcεRI-mediated cascade of events that induce an allergic response and methods for the use of these polypeptides in treating or preventing allergic disorders.

SUMMARY OF THE INVENTION

The present invention provides an isolated polypeptide, in a pharmaceutically acceptable carrier, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f).

Also provided is an isolated polypeptide, in a pharmaceutically acceptable carrier, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c).

Furthermore, the present invention provides an isolated polypeptide, which can be in a pharmaceutically acceptable carrier, produced from a cell transformed with a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f).

In addition, the present invention provides an isolated polypeptide, which can be in a pharmaceutically acceptable carrier, produced from a cell transformed with a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c).

A method of treating or preventing an allergic disorder in a subject is also provided, comprising administering the nucleic acid of the present invention to a cell of the subject under conditions whereby the nucleic acid is expressed in the subject's cells, thereby treating the allergic disorder.

The present invention also provides a fusion protein, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f), and a ligand which binds to and is internalized by cells which express a high affinity receptor for IgE on the surface.

The present invention additionally provides a fusion protein, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c) and a ligand which binds to and is internalized by cells which express a high affinity receptor for IgE on the surface.

Further provided is a fusion protein, produced from a cell transformed with a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f), and encoding a ligand which binds to and is internalized by cells which express a high affinity receptor for IgE on the surface.

In addition, the present invention provides a fusion protein, produced from a cell transformed with a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c), and encoding a ligand which binds to and is internalized by cells which express a high affinity receptor for IgE on the surface.

Finally, the present invention provides a method of treating or preventing an allergic disorder in a subject, comprising administering the fusion protein of the present invention to a cell of the subject, whereby the fusion protein treats or prevents the subject's allergic disorder.

Various other objectives and advantages of the present invention will become apparent from the following detailed description.

DETAILED DESCRIPTION OF THE INVENTION

Figure 1A:
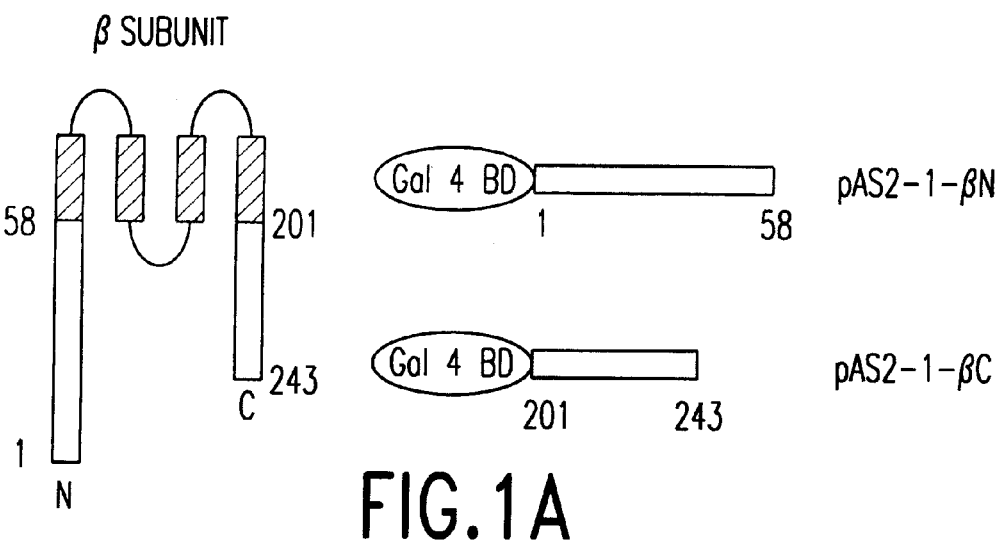
FIGS. 1A–D. Receptor and kinase proteins and the constructs used for the yeast two hybrid experiments. 1A: The β chain and the Gal 4 binding domain (BD)-receptor subunit fusion proteins based on the cytoplasmic domains of the subunit. The four transmembrane domains of the subunit are shown shaded. 1B: The γ chain and the Gal 4 binding domain-receptor subunit fusion proteins based on the cytoplasmic domain of the subunit. The transmembrane domain is shown shaded. 1C: Lyn B and the Gal 4-activation domain(ACT)-kinase fusion proteins based on the complete kinase or its unique domain. 1D: Lyn A and the Gal 4-activation domain-kinase fusion proteins based on the complete kinase or its unique domain.

As used herein, "a" can include multiples.

The present invention is based on the surprising discovery that binding of a polypeptide consisting of only the unique domain of the Lyn kinase, or portions thereof, to the C-terminal cytoplasmic domain of the β chain of the FcεRI results in inhibition of the transduction signaling activity of the FcεRI. The signaling activity of the FcεRI is triggered by binding of ligand to the extracellular domain of the receptor and aggregation of ligand-bound receptors on the cell surface of mast cells and basophils. Upon ligand binding and aggregation, the FcεRI transduces a signal across the cell membrane which initiates a cascade of events leading to release of chemical substances such as histamine, serotonin, prostaglandins and cytokines, resulting in the production of an allergic reaction in a subject. By inhibiting the initiation of this cascade of events, the release of these substances is blocked. In this manner, an allergic reaction can be treated or prevented at the level of intracellular inhibition of the production and release of allergy-inducing substances from the cells, as opposed to conventional treatment methods which attempt to block the effects of the allergy-inducing substances after they are released from activated cells. Thus, by inhibiting an allergic response at an earlier stage, the present invention provides a more efficient and effective way to treat and prevent allergic reactions than has been previously achieved.

Thus, the present invention provides an isolated polypeptide consisting of amino acids 1–66 of the tyrosine kinase, Lyn A, which can be the human Lyn A kinase and an isolated polypeptide having the amino acid sequence of SEQ ID NO:1 (human Lyn A kinase). Also provided is an isolated polypeptide consisting of amino acids 1–45 of the tyrosine kinase, Lyn B, which can be the human Lyn B kinase and an isolated polypeptide having the amino acid sequence of SEQ ID NO:2 (human Lyn B kinase).

Also provided is an isolated polypeptide, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f).

Thus, the polypeptide of this invention can comprise the amino acid sequence of 1) amino acids 1–66 of the human tyrosine kinase, Lyn A, 2) SEQ ID NO:1, 3) amino acids 1–10 of the human tyrosine kinase, Lyn A, 4) amino acids 1–27 of the human tyrosine kinase, Lyn A, 5) amino acids 27–66 of the human tyrosine kinase, Lyn A, or 6) any five or more contiguous amino acids of amino acids 1–66 of the human tyrosine kinase, Lyn A.

In addition, the present invention provides an isolated polypeptide, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c).

Thus, the polypeptide of this invention can comprise the amino acid sequence of 1) amino acids 1–45 of the human tyrosine kinase, Lyn B, 2) SEQ ID NO:2, or 3) any five or more amino acids of amino acids 1–45 of the human tyrosine kinase, Lyn B.

Also provided is an isolated nucleic acid encoding the amino acid sequence of the polypeptides described above, a vector comprising the nucleic acid and cell comprising the vector. Furthermore, the polypeptides of this invention and the nucleic acids encoding them can be in a pharmaceutically acceptable carrier.

Furthermore, the present invention provides an isolated polypeptide, in a pharmaceutically acceptable carrier, produced from a cell transformed with a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f). As used herein, "transformed" means a cell into which exogenous nucleic acid has been introduced either as naked DNA or as part of a vector.

The polypeptide of this invention can have from 80 to 100% identity with the nucleic acid sequences set forth herein and still have substantially the same biologically functional activity of the polypeptides encoded by these nucleic acids. Such variation in nucleic acid sequence among polypeptides having the same activity can be due to natural variation within a species or among species, as well as a result of modification of the amino acid sequence, as described below. The biologically functional activity of a polypeptide having between 80 and 100% identity can be determined according to the protocols for binding and inhibiting phosphorylation as described herein.

Thus, the present invention also provides a polypeptide produced from a cell transformed with a nucleic acid encoding the amino acid sequence of: 1) amino acids 1–66 of the human tyrosine kinase, Lyn A; 2). SEQ ID NO:1; 3) amino acids 1–10 of the human tyrosine kinase, Lyn A; 4) amino acids 1–27 of the human tyrosine kinase, Lyn A; 5) amino acids 27–66 of the human tyrosine kinase, Lyn A; or 6) any five or more contiguous amino acids of amino acids 1–66 of the human tyrosine kinase, Lyn A.

Also provided is an isolated polypeptide, in a pharmaceutically acceptable carrier, produced from a cell transformed with a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c).

Thus, the present invention provides a polypeptide produced from a cell transformed with a nucleic acid encoding the amino acid sequence of: 1) amino acids 1–45 of the human tyrosine kinase, Lyn B; 2) SEQ ID NO:2; or 3) any five or more contiguous amino acids of amino acids 1–45 of the human tyrosine kinase, Lyn B. As used herein, the polypeptide of this invention is the unique domain of the tyrosine kinase, Lyn A (amino acids 1–66) or Lyn B (amino acids 1–45)or any portion thereof.

Thus, the polypeptide of this invention can consist of any portion of the amino acid sequence of amino acids 1–66 of Lyn A or of the amino acid sequence of SEQ ID NO:1, as well as any portion of the amino acid sequence of amino acids 1–45 of Lyn B or of the amino acid sequence of SEQ ID NO:2. For example, the polypeptide of this invention can be amino acids 1–10 (SEQ ID NO:3), amino acids 1–27 (SEQ ID NO:4) or amino acids 27–66 (SEQ ID NO:5) of Lyn A, all of which have been demonstrated to associate with the FcεRI βc at levels greater than the negative control (consisting of Lyn A residues 27–66 out of frame (OOF).

It would be well understood by one of skill in the art that any portion of the amino acid sequence of amino acids 1–66 of Lyn A or any portion of the amino acid sequence of amino acids 1–45 of Lyn B can be identified based on the known sequence of Lyn A and Lyn B (22, 24) and produced according to methods well known in the art (e.g., peptide synthesis; expression of synthesized oligonucleotides). The portion of the amino acid sequence of Lyn A or of Lyn B can then be identified as effective in inhibiting the signaling activity of FcεRI according to the methods described in the Examples herein. Thus, the portion of the amino acid sequence of Lyn A or Lyn B which can be produced and tested for inhibitory activity according the methods of this invention can be any five or more contiguous amino acids of amino acids 1–66 of Lyn A or 1–45 of Lyn B. For example, the portion of this invention can be amino acids 1–5, 15–30, 22–45, etc., of Lyn A or Lyn B.

As used herein, "isolated" and/or "purified" means a polypeptide which is substantially free from the naturally occurring materials with which the polypeptide is normally associated in nature. Also as used herein, "polypeptide" refers to a molecule comprised of amino acids which correspond to those encoded by a nucleic acid. The polypeptides of this invention can consist of the entire amino acid sequence of amino acids 1–66 of Lyn A or of amino acids 1–45 of Lyn B or portions thereof, as set forth above. The polypeptides or portions thereof of the present invention can be obtained by isolation and purification from cells where they are produced naturally or by expression of DNA encoding amino acids 1–66 of Lyn A or amino acids 1–45 of Lyn B or portions thereof. The polypeptides of the present invention or portions thereof can be obtained by chemical synthesis of peptides, by proteolytic cleavage of the polypeptides and by synthesis from nucleic acids (either naturally occurring or synthesized) encoding the amino acid sequence of interest. The polypeptide may include conservative substitutions where a naturally occurring amino acid is replaced by one having similar properties. Such conservative substitutions do not alter the FcεRI signal transduction-inhibiting activity of the polypeptide and would be understood to include at least those listed in Table 1 (35).

Thus, it is understood that, where desired, modifications and changes may be made in the nucleic acid and/or amino acid sequence of the polypeptides of the present invention and still obtain a polypeptide having like or otherwise desirable characteristics. Such changes may occur in natural isolates or may be synthetically introduced using site-specific mutagenesis, the procedures for which, such as mis-match polymerase chain reaction (PCR), are well known in the art.

For example, certain amino acids may be substituted for other amino acids in a Lyn A or Lyn B polypeptide of this invention without appreciable loss of FcεRi signal transduction-inhibiting activity. Since it is the interactive capacity and nature of a protein that defines that protein's biological functional activity, certain amino acid sequence substitutions can be made in the Lyn A or Lyn B amino acid sequence (or, of course, the underlying nucleic acid sequence) and nevertheless obtain a Lyn A or Lyn B polypeptide of this invention with like properties. It is thus contemplated that various changes may be made in the amino acid sequence of the Lyn A or Lyn B polypeptide (or underlying nucleic acid sequence) of this invention without appreciable loss of biological utility or activity and possibly with an increase in such utility or activity.

The present invention also provides an isolated nucleic acid encoding a polypeptide consisting of amino acids 1–66 of the human tyrosine kinase, Lyn A and an isolated nucleic acid encoding a polypeptide having the amino acid sequence of SEQ ID NO:1. Also provided is an isolated nucleic acid encoding a polypeptide consisting of amino acids 1–45 of the human tyrosine kinase, Lyn B and an isolated nucleic acid encoding a polypeptide having the amino acid sequence of SEQ ID NO:2. The nucleic acids of this invention can be in a pharmaceutically acceptable carrier.

"Nucleic acid" as used herein refers to single- or double-stranded molecules which may be DNA, comprised of the nucleotide bases A, T, C and G, or RNA, comprised of the bases A, U (substitute for T), C and G. The nucleic acid may represent a coding strand or its complement. Nucleic acids may be identical in sequence to the sequence which is naturally occurring or may include alternative codons which encode the same amino acid as that which is found in the naturally occurring sequence (34). Furthermore, nucleic acids may include codons which represent conservative substitutions of amino acids as described in Table 1.

As used herein, the term "isolated" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids (33). The nucleic acids of this invention can be isolated from cells according to methods well known in the art. Alternatively, the nucleic acids of the present invention can be synthesized according to standard protocols well described in the literature.

The nucleic acid encoding the polypeptide of Lyn A or of Lyn B or portion thereof of this invention can be part of a recombinant nucleic acid comprising any combination of restriction sites and/or functional elements as are well known in the art which facilitate molecular cloning, expression and other recombinant DNA manipulations. Thus, the present invention further provides a recombinant nucleic acid comprising the nucleic acid encoding the polypeptide of Lyn A or Lyn B, or portion thereof of the present invention. In particular, the isolated nucleic acid encoding the polypeptide of Lyn A or of Lyn B or portion thereof can be present in a vector and the vector can be present in a cell, which can be a cell cultured in vitro or a cell in a transgenic animal.

Thus, the present invention further provides a vector comprising a nucleic acid encoding the polypeptide of Lyn A or of Lyn B or a portion thereof (e.g., peptides consisting of amino acids 1–10, 1–27 or 27–66 of Lyn A) of this invention. The vector can be in a pharmaceutically acceptable carrier. The vector can be an expression vector which contains all of the genetic components required for expression of the nucleic acid encoding the polypeptide of Lyn A or of Lyn B or portion thereof in cells into which the vector has been introduced, as are well known in the art. The expression vector can be a commercial expression vector or it can be constructed in the laboratory according to standard molecular biology protocols. The expression vector can comprise viral nucleic acid including, but not limited to, adenovirus, retrovirus and or adeno-associated virus nucleic acid. The nucleic acid or vector of this invention can also be in a liposome or a delivery vehicle which can be taken up by a cell via receptor-mediated or other type of endocytosis.

A polypeptide of Lyn A or of Lyn B or portion thereof of the present invention which is identified to inhibit the signaling activity of FcεRI according to the methods provided herein can be administered to a subject to treat or prevent an allergic disorder. Thus, the present invention further provides a method for treating or preventing an allergic disorder in a subject, comprising administering the nucleic acid of this invention, which encodes a polypeptide of Lyn A or of Lyn B or a portion thereof, to a cell of the subject under conditions whereby the nucleic acid is expressed in the subject's cells, thereby treating the allergic disorder.

The subject can be any animal in which it is desirable to inhibit the signal transducing activity of an immunoglobulin receptor which mediates an allergic reaction. In a preferred embodiment, the animal of the present invention is a human. In addition, non-human animals which can be treated by the method of this invention can include, but are not limited to, cats, dogs, birds, horses, cows, goats, sheep, guinea pigs, hamsters, gerbils and rabbits, as well as any other animal in which the polypeptide of the present invention can inhibit the signal transducing activity of an immunoglobulin receptor, thereby treating or preventing an allergic response.

As recited herein, an allergic disorder describes a disease state or syndrome whereby the body produces a dysfunctional immune response to environmental antigens comprising immunoglobulin E (IgE) antibodies which evoke allergic symptoms such as itching, sneezing, coughing, respiratory congestion, rhinorrhea, skin eruptions and the like, as well as severe reactions, such as asthma attacks and systemic anaphylaxis. Examples of allergic diseases and disorders which can be treated or prevented by the methods of this invention include, but are not limited to, drug hypersensitivity, allergic rhinitis, bronchial asthma, ragweed pollen hayfever, anaphylactic syndrome, urticaria, angioedema, atopic dermatitis, erythema nodosum, erythema multiforme, Stevens-Johnson Syndrome, cutaneous necrotizing venulitis, bullous skin diseases, allergy to food substances and insect venom-induced allergic reactions (36–39), as well as any other allergic disease or disorder now known or identified in the future.

As described above, the nucleic acid of the present invention can be administered in a pharmaceutically acceptable carrier and can be delivered to the subject's cells in vivo and/or ex vivo by a variety of mechanisms well known in the art (e.g., uptake of naked DNA, viral infection, liposome fusion, intramuscular injection of DNA via a gene gun, endocytosis and the like).

If ex vivo methods are employed, cells or tissues can be removed and maintained outside the body according to standard protocols well known in the art. The nucleic acids of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The cells of the subject to which the nucleic acid of this invention can be administered can include any cell which can take up and express exogenous DNA and which expresses an FcεRI whose C-terminal β chain cytoplasmic domain can be bound by the polypeptide of this invention, the binding of which results in inhibition of the signal transducing activity of the FcεRI. For example, the cells can be mast cells, basophils and/or eosinophils, as well as any other cell type which expresses an FcεRI and in which it would be desirable to inhibit the signal transducing activity of the FcεRI.

In the methods described above which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid encoding Lyn A or Lyn B polypeptide or portion thereof inside the cell. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (40, 41). The recombinant retrovirus can then be used to infect and thereby deliver to the infected cells nucleic acid encoding the polypeptide of Lyn A or of Lyn B or a portion thereof. The exact method of introducing the nucleic acid into mammalian cells is, of course, not limited to the use of retroviral vectors. Other techniques are widely available for this procedure including the use of adenoviral vectors (42), adeno-associated viral (AAV) vectors (43), lentiviral vectors (44), pseudotyped retroviral vectors (45). Physical transduction techniques can also be used, such as liposome delivery and receptor-mediated and other endocytosis mechanisms (see, for example, 46). This invention can be used in conjunction with any of these or other commonly used gene transfer methods.

As described above, the nucleic acid or vector of the present invention can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The nucleic acid or vector may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the nucleic acid or vector into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the nucleic acid or vector by inhalant can be through the nose or mouth via delivery by a spraying or droplet mechanism. Delivery can also be directly to any area of the respiratory system (e.g., lungs) via intubation. The exact amount of the nucleic acid or vector required will vary from subject to subject, depending on the species, age, weight and general condition of the subject, the severity of the allergic disorder being treated, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein (see, e.g., 47).

As one example, if the nucleic acid of this invention is delivered to the cells of a subject in an adenovirus vector, the dosage for administration of adenovirus to humans can range from about $10^7$ to $10^9$ plaque forming unit (pfu) per injection, but can be as high as $10^{12}$ pfu per injection (48, 49).

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The present invention additionally provides a fusion protein comprising a polypeptide consisting of amino acids 1–66, or a portion thereof, of the human tyrosine kinase, Lyn A or a polypeptide having the amino acid sequence of SEQ ID NO:1, or a portion thereof and a ligand which binds to and is internalized by cells which express a high affinity receptor for IgE on the surface.

Also provided is a fusion protein comprising a polypeptide consisting of amino acids 1–45, or a portion thereof, of the human tyrosine kinase, Lyn B or a polypeptide having the amino acid sequence of SEQ ID NO:2, or a portion thereof and a ligand which binds to and is internalized by cells which express a high affinity receptor for IgE on the surface.

The present invention further provides a fusion protein, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f), and a ligand which binds to and is internalized by cells which express a high affinity receptor for IgE on the surface.

The fusion protein of the present invention can comprise a polypeptide comprising the amino acid sequence of: 1) amino acids 1–66 of the human tyrosine kinase, Lyn A, 2) SEQ ID NO:1, 3) amino acids 1–10 of the human tyrosine kinase, Lyn A, 4) amino acids 1–27 of the human tyrosine kinase, Lyn A, 5) amino acids 27–66 of the human tyrosine kinase, Lyn A, or 6) any five or more contiguous amino acids of amino acids 1–66 of the human tyrosine kinase, Lyn A, and a ligand which binds to and is internalized by cells which express a high affinity receptor for IgE on the surface.

Further provided is a fusion protein, comprising a polypeptide having an amino acid sequence encoded by a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c) and a ligand which binds to and is internalized by cells which express a high affinity receptor for IgE on the surface.

The fusion protein of the present invention can comprise a polypeptide comprising the amino acid sequence of: 1) amino acids 1–45 of the human tyrosine kinase, Lyn B, 2) SEQ ID NO:2, or any five or more contiguous amino acids of amino acids 1–45 of the human tyrosine kinase, Lyn B, and a ligand which binds to and is internalized by cells which express a high affinity receptor for IgE on the surface.

Additionally, the present invention provides a fusion protein, produced from a cell transformed with a nucleic acid which is at least 95% identical to a nucleic acid selected from the group consisting of: a) a nucleic acid encoding a polypeptide having the amino acid sequence of amino acids 1–66 of the human tyrosine kinase, Lyn A; b) a nucleic acid encoding a polypeptide having the amino acid sequence of SEQ ID NO:1; c) a nucleic acid encoding a polypeptide having amino acids 1–10 of the human tyrosine kinase, Lyn A; d) a nucleic acid encoding a polypeptide having amino acids 1–27 of the human tyrosine kinase, Lyn A; e) a nucleic acid encoding a polypeptide having amino acids 27–66 of the human tyrosine kinase, Lyn A; and f) a nucleic acid encoding a polypeptide having any five or more contiguous amino acids of amino acids 1–66 of the human tyrosine kinase, Lyn A, wherein the polypeptide has substantially the same biologically functional activity of the polypeptide encoded by the nucleic acid sequence as set forth in (a), (b), (c), (d), (e) or (f), and encoding a ligand which binds to and is internalized by cells which express a high affinity receptor for IgE on the surface.

The fusion protein of the present invention can comprise a polypeptide produced by a cell transformed with a nucleic acid encoding the amino acid sequence of: 1) amino acids 1–66 of the human tyrosine kinase, Lyn A, 2) SEQ ID NO:1, 3) amino acids 1–10 of the human tyrosine kinase, Lyn A, 4) amino acids 1–27 of the human tyrosine kinase, Lyn A, 5) amino acids 27–66 of the human tyrosine kinase, Lyn A, or 6) any five or more contiguous amino acids of amino acids 1–66 of the human tyrosine kinase, Lyn A, and a ligand which binds to and is internalized by cells which express a high affinity receptor for IgE on the surface.

In addition, the present invention provides a fusion protein, produced from a cell transformed with a nucleic acid which is at least 95% identical to a nucleic acid selected from the group consisting of: a) a nucleic acid encoding a polypeptide having the amino acid sequence of amino acids 1–45 of the human tyrosine kinase, Lyn B; b) a nucleic acid encoding a polypeptide having the amino acid sequence of SEQ ID NO:2; and c) a nucleic acid encoding a polypeptide having any five or more amino acids of amino acids 1–45 of the human tyrosine kinase, Lyn B, wherein the polypeptide has substantially the same biologically functional activity of the polypeptide encoded by the nucleic acid sequence as set forth in (a), (b) or (c), and encoding a ligand which binds to and is internalized by cells which express a high affinity receptor for IgE on the surface.

The fusion protein of the present invention can comprise a polypeptide produced by a cell transformed with a nucleic acid encoding the amino acid sequence of: 1) amino acids 1–45 of the human tyrosine kinase, Lyn B, 2) SEQ ID NO:2, or 3) any five or more contiguous amino acids of amino acids 1–45 of the human tyrosine kinase, Lyn B, and a ligand which binds to and is internalized by cells which express a high affinity receptor for IgE on the surface.

The ligand of the fusion protein can be any ligand which has the capability of binding to and becoming internalized by cells which express FcεRI or its equivalent in other species, as determined by methods well known in the art. For example, the ligand of the fusion protein of this invention can be IgE or portions thereof which can bind a receptor, c-Kit or portions thereof which can bind a receptor, or any other ligand or portion thereof which can bind to and become internalized by cells which express a high affinity receptor for IgE on the surface.

The present invention further provides a nucleic acid encoding the fusion protein of this invention, a vector comprising the nucleic acid and a cell comprising the vector. The present invention also provides nucleic acids complementary to, or capable of, hybridizing with the nucleic acids encoding the fusion proteins of this invention. The fusion protein and the nucleic acid encoding it can be in a pharmaceutically acceptable carrier.

Protocols for construction of a vector containing a nucleic acid encoding the fusion protein of this invention are well known in the art (see, e.g., 60). For example, nucleic acid encoding a Lyn A or Lyn B polypeptide or portion thereof of this invention can be ligated to a nucleic acid encoding the ligand of this invention according to standard molecular biology protocols such that a continuous open reading frame results which will allow for production of the fusion protein. The nucleic acids can be obtained from naturally occurring sources or the nucleic acids can be synthesized. The nucleic acid encoding the fusion protein can be placed into an expression vector, which can be obtained commercially or produced in the laboratory.

A variety of vectors and eukaryotic expression systems such as yeast, filamentous fungi, insect cell lines, bird, fish, transgenic plant and mammalian cells, among others, are known to those of ordinary skill in the art and can be used in the present invention.

Thus, the present invention further contemplates a method of producing the fusion protein of the present invention, comprising introducing a vector encoding the fusion protein into a eukaryotic cell under conditions whereby the nucleic acid encoding the fusion protein is expressed and the fusion protein is produced; and isolating and purifying the fusion protein. Isolation and purification of the fusion protein can be carried out by protocols well known to those of skill in the art.

The nucleic acid sequences can be expressed in cells after the sequences have been operably linked to, i.e., positioned, to ensure the functioning of an expression control sequence. These expression vectors are typically replicable in the cells either as episomes or as an integral part of the cell's chromosomal DNA. Commonly, expression vectors can contain selection markers, e.g., tetracycline resistance, hygromycin resistance, gentamicin resistance or methotrexate resistance, to permit detection and/or selection of those cells transformed with the desired nucleic acid sequences (see, e.g., U.S. Pat. No. 4,704,362).

The cells are rendered competent for transformation by various means known in the art. There are several well-known methods of introducing DNA into eukaryotic cells. These include, but are not limited to, calcium phosphate precipitation, fusion of the recipient cells with bacterial protoplasts containing the DNA, treatment of the recipient cells with liposomes containing the DNA, DEAE dextran, electroporation, micro-injection of the DNA directly into the cells, as well as any other technique now known or developed in the future for introducing nucleic acid into cells.

The transformed cells are cultured by means well known to one of ordinary skill in the art (54). The expressed polypeptides are isolated from cells grown as suspensions or monolayers. The latter are recovered by well-known mechanical, chemical, or enzymatic means and purified according to standard methods well known in the art.

The vector of the invention, e.g., a plasmid, which is used to transform the host cell, preferably contains nucleic acid sequences to initiate transcription and sequences to control the translation of the protein. These sequences are referred to as expression control sequences. Suitable vectors for expression systems usually have expression control sequences, such as promoters, including 3-phosphoglycerate kinase or other glycolytic enzymes, an origin of replication, termination sequences and the like, as desired. Preferred expression control sequences are promoters derived from immunoglobulin genes, SV40 virus, adenovirus, bovine papilloma virus, etc, as are well known in the art. For example, gene sequences to control replication in the host cell may be incorporated into the vector such as those found in bovine papilloma virus-type vectors (50). A variety of suitable vectors are described in the literature (51, 52).

Appropriate vectors for expressing proteins in insect cells are usually derived from baculovirus. Suitable insect cell lines include, but are not limited to, mosquito larvae, silkworm, armyworm, moth and Drosophila cell lines such as a Schneider cell line (54), as well as any other insect cell line now known or identified in the future to be a suitable host cell line for baculovirus or other insect cell expression vectors.

When yeast or higher animal host cells are employed, polyadenylation or transcription terminator sequences from known mammalian genes can be incorporated into the vector. An example of a terminator sequence is the polyadenylation sequence from the bovine growth hormone gene. Sequences for accurate splicing of the transcript may also be included. An example of a splicing sequence is the VP1 intron from SV40 (53).

Synthesis of heterologous proteins in yeast is well known. For example, Sherman et al. (55), is a well-recognized work describing the various methods available to produce a protein in yeast. Two procedures are used in transforming yeast cells. In one case, yeast cells are first converted into protoplasts using zymolase, lyticase, or glusulase, followed by addition of DNA and polyethylene glycol (PEG). The PEG-treated protoplasts are then regenerated in a 3% agar medium under selective conditions. Details of this procedure are described by Beggs, J. D. (59) and Hinnen et al. (56). The second procedure does not involve removal of the cell wall. Instead, the cells are treated with lithium chloride or acetate and PEG and put on selective plates (57). The fusion proteins of this invention, once expressed, can be isolated from yeast by lysing the cells and applying standard protein isolation and purification techniques to the lysates. The monitoring of the purification process can be accomplished by using Western blot techniques or radioinimunoassay or other standard immunoassay techniques.

Expression of nucleic acid encoding exogenous proteins can also be carried in a variety of mammalian cell lines. Mammalian cells permit the expression of proteins in an environment that favors important post-translational modifications such as folding and cysteine pairing, addition of lipids (including myristate and palmitate), addition of complex carbohydrate structures and secretion of active protein.

Mammalian cell systems can be in the form of monolayers of cells, although mammalian cell suspensions may also be used. A number of suitable host cell lines capable of expressing intact proteins have been developed in the art, and include the HEK293, BHK21, COS and CHO cell lines, as well as various human cells such as HeLa cells, myeloma cell lines, Jurkat cells, etc., as are known in the art. Other animal cells useful for the production of proteins are available, for example, from the American Type Culture Collection Catalogue of Cell Lines and Hybridomas (7th Edition, 1992). Expression vectors for these cells can include expression control sequences, such as an origin of replication, a promoter (e.g., the CMV promoter, a HSC tk promoter or pgk [phosphoglycerate kinase] promoter), an enhancer (58) and necessary processing information sites, such as ribosome binding sites, RNA splice sites, polyadenylation sites (e.g., an SV40 large T antigen poly A addition site) and transcriptional terminator sequences.

The fusion protein of this invention can also be expressed in transgenic plant expression systems known in the art, such as, for example, soy bean cells or *Nicotiana tabacum* cells (63).

It is also contemplated that the nucleic acids encoding the fusion proteins of the present invention can be used to generate transgenic nonhuman animals in which the nucleic acid encoding a fusion protein of the present invention is added to the germ line of the animal. Thus, a cell of the invention containing an nucleic acid of this invention is contemplated to include a cell in a transgenic animal. The plant holotoxin or fusion protein can be isolated and purified from materials secreted by the animal, such as for example, milk secreted from nonhuman mammals. Transgenic animals are generated by standard means known to those skilled in the art (see, for example, 64).

The fusion protein of the present invention can be in a pharmaceutically acceptable carrier, as defined herein and can be administered to a subject according to the same protocols for dosage determination, modes of administration and efficacy determination as set forth above regarding the administration of the nucleic acid of this invention to a subject.

Thus, a method of treating or preventing an allergic disorder in a subject is also provided, comprising administering an effective amount of the fusion protein of the present invention to a cell of the subject, whereby the fusion protein treats or prevents the subject's allergic disorder. In a preferred embodiment, as set forth above, the subject is a human, but can be any animal in which it is desirable to treat or prevent an allergic disorder. Also, the preferred mode of administration of the fusion protein is intranasally or in an inhalant and the cells to which the fusion protein is administered are preferably mast cells and basophils.

It is contemplated that fusion protein of this invention may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the fusion protein into the nose and nasal passages through one or both of the nares and can comprise delivery by a spraying mechanism or droplet mechanism, or through aerosolization of the fusion protein. The latter may be effective when a large number of animals is to be treated simultaneously. Administration of the fusion protein by inhalant can be through the nose or mouth via delivery by a spraying or droplet mechanism. Delivery can also be directly to any area of the respiratory system (e.g., lungs) via intubation. The exact amount of the fusion protein required will vary from subject to subject, depending on the species, age, weight and general condition of the subject, the severity of the allergic disorder being treated, the particular fusion protein used, its mode of administration and the like. Thus, it is not possible to specify an exact amount for every fusion protein. However, an appropriate amount can be determined by one of ordinary skill in the art using only routine experimentation given the teachings herein (see, e.g., 47).

Parenteral administration of the fusion protein of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

In the methods of the present invention which describe the treatment of an allergic disorder with either a nucleic acid or protein, the efficacy of the treatment can be monitored according to clinical protocols well known in the art for monitoring the treatment of allergic disorders. For example, such clinical parameters as allergy symptoms (itching, sneezing, coughing, respiratory congestion, rhinorrhea, skin eruption, etc.), assays and skin prick tests (wheal and flare response) to known allergans and serum levels of IgE and allergy-associated cytokines (e.g., interleukin-4, interleukin-5) can be monitored for determining efficacy. Indicators of efficacy of the treatment can include a reduction in severity and/or absence of symptoms, an increase in the number of symptom-free days per time period (e.g., per month) and/or a reduction in the need for conventional medications such as decongestants, anti-histamines, mast cell stabilizers and corticosteroids. Additionally, if the treatment of this invention is done in conjunction with immunotherapy, efficacy can be evaluated by observing an increase in tolerated dose of the subject's known allergan(s). These parameters can be monitored weekly or monthly, as well as at greater time intervals (e.g., every 3–6 months). In a particular example, clinical parameters that can be monitored for asthma can include the number and severity of attacks as determined by symptoms of wheezing, shortness of breath and coughing. The measurement of airway resistance by the use of respiratory spirometry, the extent of disability and the dependence on immunosuppressive medications or bronchodilators can also be determined (61, 62).

Additionally, the efficacy of administration of the nucleic acid or fusion protein of this invention for preventing an allergic disorder in a subject not known to have an allergic disorder, but known to be at risk of developing an allergic disorder, can be determined by evaluating clinical parameters such as allergy symptoms (itching, sneezing, coughing, respiratory congestion, rhinorrhea, skin eruption, etc.), assays and skin prick tests (wheal and flare response) to known allergans and serum levels of IgE and allergy-associated cytokines (e.g., interleukin-4, interleukin-5), over time following administration of the nucleic acid or fusion protein of this invention. This time interval can be very short (i.e, minutes/hours) or very long (i.e., years/decades). The determination of who would be at risk for the development of an allergic disorder would be made based on current knowledge of the known risk factors for a particular allergic disorder as would be familiar to clinicians and researchers in this field, such as a particularly strong family history of an allergic disorder or exposure to or acquisition of factors or conditions (i.e., environmental) which are likely to lead to development of an allergic disorder.

In addition, it would be well understood by the artisan that, on the basis of the surprising discovery of the present invention, the binding domains of other kinases which bind the cytoplasmic domains of receptors involved in signal transduction can be screened for the ability to inhibit signal transduction by the receptor in the same manner by which the polypeptide of Lyn A and Lyn B of this invention inhibit the signal transduction activity of FcεRI. Thus, the present invention also contemplates a method of screening polypeptides of kinases for the ability to inhibit signal transduction by a receptor having a cytoplasmic domain to which the kinase binds comprising producing a polypeptide having the amino acid sequence of a portion of the kinase; determining whether the polypeptide binds the cytoplasmic domain of the receptor according to the methods herein and determining whether the polypeptide, which is identified as binding the cytoplasmic domain of the receptor, inhibits the signal transducing activity of the receptor according to the methods herein, thereby identifying a polypeptide of a kinase as having the ability to inhibit signal transduction by the receptor.

The present invention is more particularly described in the following examples which are intended as illustrative only since numerous modifications and variations therein will be apparent to those skilled in the art.

EXAMPLES

Materials. The yeast strains (CG1945 and Y187) and cloning vectors (pAS2-1 and pACT) were obtained from Clontech (Palo Alto, Calif.); the expression vectors pBlueBac, pCDM8 and pZeo, as well as a baculovirus MAXBAC expression kit were obtained from InVitrogen (Carlsbad, Calif.); polyacrylamide gels used for electrophoresis (PAGE) was obtained from NOVEX (San Diego, Calif.); the antibiotics (G418, zeocin) were obtained from Life Technologies (Gaithersburg, Md.) and InVitrogen, respectively and plasmid DNA purification kits were obtained from Qiagen (Santa Clarita, Calif.).

Antibodies. Monoclonal anti-phosphotyrosine antibodies conjugated to horseradish peroxidase (anti-PY) were obtained from Transduction Labs (PY-20, Lexington, Ky.) or UBI (4G10; Lake Placid, N.Y.). Polyclonal antibodies to human src-family kinases, Lyn and Fyn, were purchased from UBI and polyclonal antibodies to c-Src and c-Yes were obtained from Santa Cruz Biotechnology (Santa Cruz, Calif.). Mouse monoclonal anti-DNP IgE (12) and rat IgE (of unknown specificity) (13) were purified as described previously (14, 15) and labeled with carrier-free [$^{125}$I] using chloramine T (16). Goat anti-mouse IgE was purchased from ICN (Costa Mesa, Calif.); rabbit anti-rat IgE was purified as described (17). Covalently cross-linked IgE oligomers were prepared and analyzed as described (6).

Cell Lines. Rat Basophilic Leukemia (RBL-2H3) cells were maintained as previously described (18). Chinese Hamster Ovary (CHO) cells were grown in stationary flasks at 37° C. in a humidified atmosphere containing 5% $CO_2$ in Iscove's Modified EMEM, 10% fetal calf serum, 25 mM HEPES and the appropriate antibiotics to maintain expression of the transfected genes. Spodoptera frugiperda (Sf9) insect cells were maintained in spinner culture at 27° C. as previously described (19).

DNA Sequencing. The nucleotide sequence of each expression construct was confirmed by automated DNA sequencing using a dye terminator kit obtained from Applied Biosystems (Foster City, Calif.).

Isolation of Rat Lyn Kinase cDNAs. A 5' stretch cDNA library was prepared from mRNA isolated from RBL cells. Two separate priming reactions with either oligo(dT) or random primers were performed to generate the first strand. The reactions were pooled prior to second strand synthesis. The cDNA library was then prepared in the expression vector pCDM8 (20). Probes were prepared by restriction digestion of human Lyn A-pSVL. Probes representing the N-terminus (amino acid residues 1–298) and the C-terminus (residues 163–512) (22) were purified. The library was plated and colony lifts were hybridized with either probe. Positive colonies went through secondary and tertiary screening. The nucleotide sequence of two clones, designated N14 (2052 bp) and C18 (2316 bp), was determined by primer walking and DNA sequencing of both strands. The Wisconsin Package from the Genetics Computer Group, Inc. was used to assemble and analyze the nucleotide sequences of the isolated clones. N14 contained an open reading frame of Lyn A, beginning with ATG from bp 80 to bp 1616 while clone C18 encoded Lyn B beginning with ATG between bp 236 and bp 1709. The sequence of Lyn A in the coding region was identical to a previously published sequence (21); the sequence of rat Lyn B lacks an "insert" of 21 amino acids found in the A form of the kinase at a position identical to that previously shown for human and murine Lyn (22, 23) but is otherwise identical to Lyn A. Therefore it differs somewhat from the previously published sequence for rat Lyn B (24).

CHO cells were transiently transfected with the Lyn-pCDM8 plasmids by electroporation, harvested 48–72 hours later and a lysate of the whole cells was prepared using SDS. After separation by PAGE and transfer, Western blotting with anti-human Lyn confirmed that the expressed proteins had the expected the size for Lyn A (56 kD) and Lyn B (53 kD).

Yeast Two-hybrid Fusion Constructs. To generate DNA binding domain fusion proteins, the N terminal (1–58) and C-terminal (201–243) cytoplasmic domains of the rat FcεRIβ (65) were amplified by polymerase chain reaction (PCR) from the full length cDNA and cloned into the EcoRI/BamHI sites of pAS2-1. The cytoplasmic domain of rat FcεRIγ (residues 27–68), as a PCR fragment, was cloned into Nco I/Bam HI site of pAS2-1, to generate pAS2-1-γC. To create activation domain fusion proteins, the full length Lyn A and Lyn B and various deletion mutants were amplified by PCR and cloned into Bam HI/Xho I sites of pACT.

Yeast Two-hybrid Co-transformation, Selective Growth and β-Galactosidase Assays. Plasmid constructs were introduced into yeast cells by lithium acetate, following the protocol provided by Clontech. Transformants were plated on synthetic medium containing 5 mM 3-amino-1,2,4-trizole and lacking leucine, tryptophan and histidine (SD-3) to detect the His phenotype, or synthetic medium lacking leucine and tryptophan (SD-2), to measure transformation efficiency. The β-galactosidase activity of transformants was measured in a filter assay with X-gal as substrate or in a liquid assay with an ONPG substrate according to the Clontech protocol.

Mammalian Transfection Constructs. The 2.3 kb LynB Xho I-digested insert was isolated from pCDM8 and subcloned into the Xho I site of pZeo. The unique domain construct was generated by PCR amplification using internal sense and antisense primers for the unique domain: 5'-CGGGCGGCTCGATGGGATGTATTAAATCAAAA AGGAAAG-3' (SEQ ID NO:6), and 5'-CGGCGGCTCGAGCTAGTCCCCTTGCTCCTCTG GATC-3' (SEQ ID NO:7), respectively.

The final PCR product was digested with Xho I and cloned back into the pZeo Xho I site. The catalytically inactive Lyn B(K279R)-pZeo construct was prepared using the Altered Sites in vitro Mutagenesis System from Promega (Madison, Wis.) as follows: A 2.3 kb Xba I fragment of Lyn B from Lyn-pCDM8 was ligated into the Xba I site of pAlter-1. Mutagenesis was carried out according to the manufacturer's protocol, using the ampicillin repair primer provided in the kit and a Lyn single mutation antisense oligo: (5'-GCCAGGCTTGAGGGTC CTTACAGCCACTTTTGTGC-3') (SEQ ID NO:8) to convert T$\underline{T}$C (Lys) → TCC (Arg). The mutant Lyn B was digested with Xho I and BstB I and ligated back into pZeo.

Transfection of CHO Cells. Using Lipofectin reagent-mediated transfection (Life Technologies), pSVL constructs of the α, β and γ subunits of rat FcεRI, along with pSV2neo had been previously introduced into CHO cells and a clone expressing a high number of receptors was frozen. After thawing, expression of receptors decreased rapidly with time in culture so the culture was re-cloned by incubating the cells with fluorescein-conjugated IgE and sorting on a fluorescence activated cell sorter. The 1% of cells expressing the highest number of receptors were re-sorted on 96-well plates at 0.5/cell per well. Fifty surviving clones were screened for expression of receptors by growing the cells to confluence and sensitizing them with [$^{125}$I]-mouse IgE. The washed, adherent cells were solubilized with boiling SDS sample buffer and the IgE in the extract was quantitated by γ-counting. Of five high expressing clones, one (CHO-B12) proved highly stable and was used for all subsequent studies. CHO-B12 cells were cryopreserved by freezing in 5% dimethylsulfoxide/95% growth media (higher concentrations of dimethylsulfoxide caused a rapid decline in FcεRI). The cells were electroporated (0.4 cm gap cuvettes, 200 V, 500 μF) in the presence of one of several rat Lyn-pZeo constructs or empty pZeo vector which had been linearized by digestion with Eco 57I. To select resistant clones, the media was supplemented with 250 μg/ml zeocin at 72 hr post transfection.

Baculovirus expression of human Lyn B. The human Lyn B cDNA (1.5 Kb) was excised from pSVL by Xba I digestion and ligated into the homologous Nhe I site of pBlueBac. Sf9 cells were co-transfected with wild type AcMNPV DNA and the Lyn construct to generate recombinant Lyn baculoviruses. Adherent Sf9 cells were infected with plaque-purified baculovirus at a multiplicity of infection of 0.4. After 48 hrs, the cells were lysed in 0.1% NP-40 buffer containing protease and phosphatase inhibitors. Western blotting with anti-PY indicated that the Lyn B protein was phosphorylated on tyrosine as it was produced in the insect cells.

Stimulation of Cells. CHO cells to be stimulated with antigen were sensitized overnight with [$^{125}$I]-labeled mouse anti-DNP mouse IgE, washed thrice in buffer A (150 mM NaCl/5 mM KCl/25 mM Pipes, pH 7.2) plus 0.1% (w/v) gelatin and 5.4 mM dextrose and resuspended at 1×10$^7$ cells per ml. DNP6-BSA was added as a 5× stock solution to 5×10$^6$ cells at 37° C. for various time periods. CHO cells stimulated with IgE oligomers were incubated with various concentrations at 37° C. for various time periods.

Solubilization and Immunoprecipitation. After stimulation, the receptors were solubilized in 0.05% Triton X-100 (3). For immunoprecipitation, anti-mouse or anti-rat IgE antibody was pre-bound to 30 μl protein A-sepharose beads overnight in borate-buffered saline, pH 8, containing 0.1% gelatin. The beads were recovered by centrifugation and combined with the lysates ("pre-cleared" with 100 μl protein A-sepharose beads overnight) for two hours. After re-centrifnigation, the immunoprecipitates were washed four times as previously described (3) and the bound proteins were released by boiling in SDS sample buffer for five minutes.

Quantitation of Phosphorylation of Receptors. Immunoprecipitated receptors were separated by electrophoresis in SDS on 10% polyacrylamide gels equilibrated with Tricine and the phosphorylated proteins were detected with an anti-PY antibody and an Enhanced Chemiluminescent detection system (Amersham, Arlington Heights, Ill.) (25). Autoradiographs of Western blots were quantitated by computerized densitometry (Molecular Dynamics, Sunnyvale, Calif.). Three steps were taken to ensure equal numbers of receptors were being compared in those studies in which cells co-transfected with inactive forms of Lyn were compared to cells that had not been co-transfected. First, the cells were incubated with IgE that had been labeled with [$^{125}$I] and equal numbers of counts were loaded per lane. Second, one lane on each gel was loaded with the same amount of phosphorylated human Lyn B to correct for differences in transfer, antibody staining, washing, etc. Third, the primary anti-PY blots were stripped and reprobed with an antibody (JRK) to the β chain of the receptor (26) and densitometric analysis was repeated. The densitometric values from the primary anti-PY blots were then corrected for any differences in anti-PY staining or loading of receptors. In separate experiments, the linearity of antibody staining (anti-PY, anti-β) was verified by loading increasing amounts of an appropriate protein extract and quantitating the band intensity.

Quantitation of Lyn. To quantitate the relative amounts of Lyn, whole cell lysates containing either 7×10$^4$ or 1.6×10$^5$ cell equivalents were prepared with SDS for each transfectant. Depending on which molecules had been transfected, the samples were separated on 8% (Lyn B, RK Lyn), 10% (CHO-B12, pZeo) or 4–20% (unique Lyn A) Tris-Glycine gels and blotted with an anti-Lyn antibody and an HRP-conjugated anti-rabbit secondary antibody. One lane on each gel was loaded with a fixed amount of human Lyn B (above). The densitometric readings for the bands corresponding to Lyn were normalized relative to the human Lyn B standard.

Quantitation of FcεRI. CHO cells were suspended at a concentration of 510$^6$ per ml and incubated with 5 μg/ml of

[$^{125}$I]-labeled IgE for one hour at 37°. Nonspecific binding was evaluated by preincubating the cells with a 10-fold excess of unlabeled IgE for 30 minutes at 37°. Cells were separated from unbound IgE by pelleting through phthalate oil (15, 27).

Subcellular Fractionation. CHO cells were sonicated and the 140,000× g supernatant (cytosolic fraction) and pellet (membrane fraction) were prepared from the post-nuclear supernatant as previously described (28). Membrane proteins were solubilized in 0.5% Triton X-100 for 30 minutes at 4° C. Each subcellular fraction was treated with an equal volume of boiling 2× SDS sample buffer for five minutes prior to gel electrophoresis.

In vitro transcription/translation. Coupled in vitro transcription-translation reactions were conducted with [$^{35}$S]-Cys according to the manufacturer's recommendation (T3 TnT® Coupled Reticulocyte Lysate Systems, Promega). The reaction mixture contains $Mg^{2+}$, ATP and NaCl in a neutral pH buffer and can support a kinase reaction.

Figure 1B:
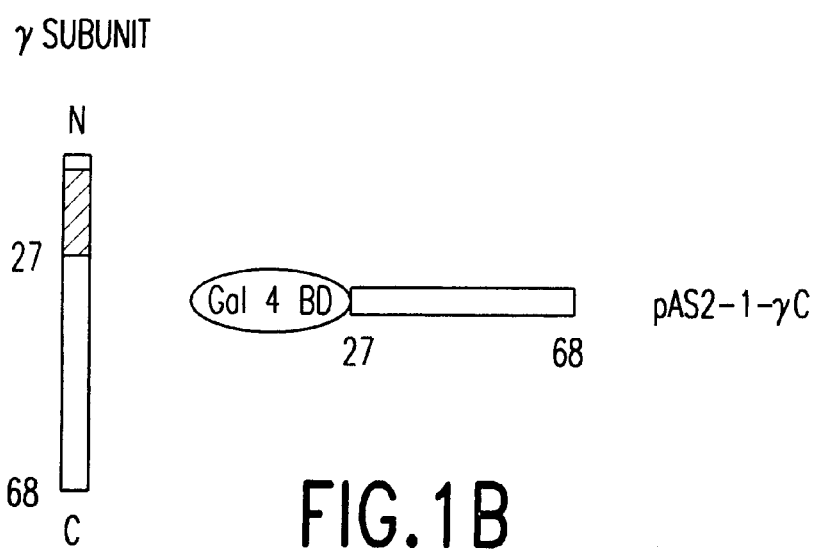
Figures 1C, 1D:
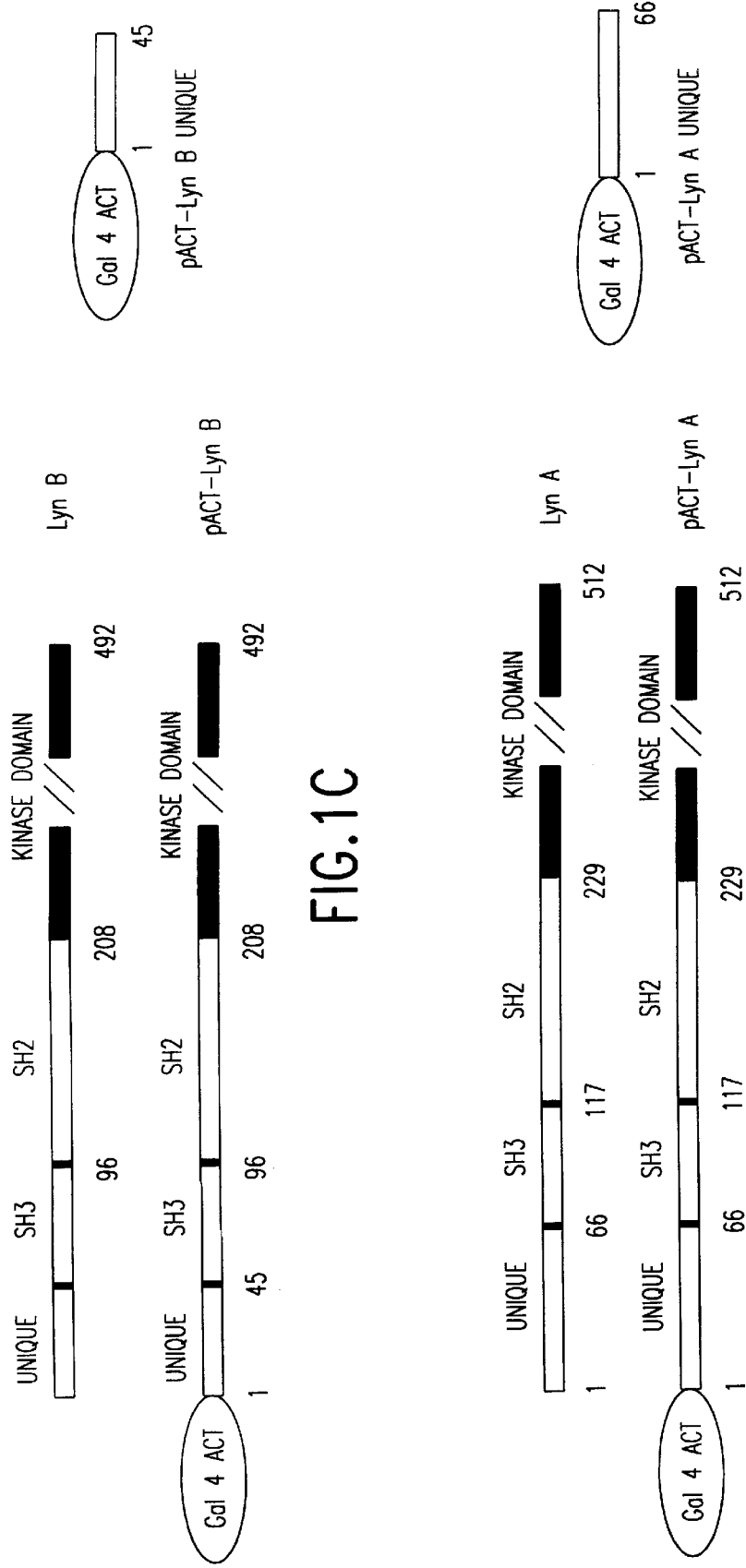

Yeast Two-hybrid Studies. Initial identification of potentially interacting domains was conducted by co-transforming constructs containing the cytoplasmic domains of the FcεRI fused to the binding domain of the Gal 4 transcription factor with constructs containing Lyn or various mutated forms of Lyn fused to the activation domain of Gal 4 (11) (FIG. 1).

The nucleotide sequence coding for the amino- and carboxy-terminal cytoplasmic domains of the β subunit of the rat IgE receptor, $β_N$ and $β_C$, respectively, were subcloned into pAS2 to generate Gal 4 DNA binding domain fusion proteins. Unfortunately, both fusion proteins autonomously activated the reporter genes. This is presumably due to the acidic hemagglutinin epitope located between the Gal4 DNA binding domain and the inserted proteins (29). However, the fusion protein containing the cytoplasmic domain of the γ subunit was not autonomously active. Therefore, nucleotide sequences coding for $β_N$ and $β_C$ were subcloned into the newly developed vector, pAS-2-1, which is similar to pAS2, but has the acidic hemagglutinin epitope removed. Neither pAS2-1-$β_C$ or pAS2-1-$β_N$ were autonomously active.

The activities of the His and LacZ reporter genes in CG1945 yeast transformants expressing Lyn and $β_N$, $β_C$ or γC were tested as described herein. Both the full length and unique domain of both Lyn A and Lyn B interacted directly with $β_C$. However, the interaction was much weaker than the interaction detected between the p53 and SV40 fusion proteins used as a positive control. Thus, per µg DNA, co-transformation with p53 and SV40 resulted in more colonies on His-deficient medium (SD-3) and rapid growth into large colonies. All of the colonies containing p53 and SV40 rapidly turned blue. In contrast, co-transformation with the Lyn and $β_C$ constructs resulted in fewer colonies and slower growth on His-deficient medium and only the large colonies turned blue. No interaction was detected between $β_N$ or $γ_C$ with any forms of Lyn in this assay.

To quantitate the interaction between Lyn and $β_C$ or $β_N$, the β-galactosidase activity of these co-transformants in yeast strain Y187 was measured in a liquid assay. In addition to the full-length Lyn and the construct containing only the unique domain, a series of Lyn mutants was tested on the basis of results of Pleiman, et al. (30) and Timson Gauen et al. (31). The negative control in this experiment was the 40 amino acid residues (from 27 to 66; SEQ ID NO:5) of Lyn A fused out-of-frame to the Gal 4-AD (pACT-27-66-OOF). These studies showed that the activity of the LacZ reporter gene from co-transformants with the unique domain of either Lyn A or B was as high as the activity from co-transformants with the full-length form of either Lyn. These values are three-fold higher than those from the negative control pACT-27-66-OOF. Consistent with the result from CG1945 strain, the interaction between Lyn and $β_C$ is weaker (on the basis of the β-galactosidase activity, only 1 per cent as strong) than that between p53 and SV40. Co-transformants containing Lyn amino acid residues 1–10, 1–27 or 27–66 produced slightly higher amounts of β-galactosidase than the negative control. No interaction between Lyn and $β_N$ was detected.

Characterization of Transfected FcεRI in CHO Cells. A clone of transfected CHO cells that stably expressed ~170,000 receptors per cell (CHO-B12) (Table 2) was further characterized. When immunoblotted with anti-human Lyn antibody, extracts of these cells, like those of the untransfected CHO cells, show a weakly reactive component at ~58 kDa, i.e., slightly greater than the apparent molecular mass of 53 and 56 kDa observed for rat Lyn. There was no reactivity with a panel of antibodies to human c-Src, Fyn or c-Yes. Cells from the B12 clone were incubated with anti-DNP-specific mouse IgE and, after solubilization with detergent, the bound (unaggregated) receptors were immunoprecipitated with goat anti-mouse IgE. Upon western blotting with anti-PY, no evidence for phosphorylation was observed. When the cells were incubated with multivalent antigen (DNP-BSA) prior to solubilization, phosphorylation of tyrosines on the β and γ subunits of the transfected receptors was observed. Disaggregation of the receptors in vivo by addition of hapten (DNP-caproic acid) after the exposure to DNP-BSA led to the complete reversal of the antigen-induced phosphorylation of receptor tyrosines within <1 minute.

RBL cells can be stimulated either by aggregating receptor-bound monomeric IgE with antigen or by incubating the cells with preformed dimers of IgE. In contrast, incubation of CHO-B12 cells with dimeric IgE failed to induce detectable phosphorylation of the receptors. These results are consistent with a limiting amount of protein tyrosine kinase being associated with the receptors in these cells.

Correlation Between Total Lyn and Phosphorylation of FcεRI. A series of stable transfectants of the CHO-B12 cells with rat Lyn were isolated. The relative ratios of full-length Lyn/receptor of six clones (A6 through D8) are shown in the upper part of column 5 of Table I. Subcellular fractionation of the transfected cells indicated that the transfected full-length Lyn was expressed as a membrane-associated protein, as expected for a Src-family kinase (32).

The various transfectants were stimulated either with IgE dimers or with monomeric IgE, followed by antigen, to examine the relationship between the total cellular content of Lyn and the responsiveness of the cells. Care was taken to ensure equal numbers of receptors were being compared.

A good correlation between the amount of Lyn expressed and the amount of receptor tyrosine phosphorylation was seen with both the β and γ subunits upon aggregation of the receptors with antigen. Furthermore, all of the cells expressing transfected Lyn now responded to dimers of IgE. More extensive phosphorylation was observed in those cells whose receptors were aggregated with antigen rather than with dimers. However, the stimulation by dimers was more sensitive to the amount of Lyn expressed.

One clone, A11, in which the relative Lyn/receptor ratio was exceptionally high, showed a significant degree of phosphorylation of the receptors even without stimulation.

Western blotting of A11 lysates revealed a phosphorylated component with an apparent molecular mass of 53 kDa (presumably Lyn), but no change in overall phosphorylation of tyrosines on other cellular proteins when compared to CHO-B12 lysates.

To control for differences in tyrosine phosphorylation that may have arisen due to zeocin resistance alone, CHO-B12 cells were transfected with pZeo vector and resistant colonies were isolated and expanded. Upon stimulation with 0.5 µg/ml trimeric IgE from 5 to 30 minutes, the six zeocin resistant clones tested showed no significant differences in phosphorylation of the β and γ subunits of the receptor as compared to CHO-B12 cells. In a similar experiment, the responses to varying doses of antigen (25–300 ng/ml) of three zeocin-resistant clones were compared to CHO-B12 cells. A similar dose-dependence of phosphorylation of the receptors was observed. No differences were noted in either the magnitude or pattern of total cellular proteins that became tyrosine phosphorylated. By Western blotting, the level of endogenous Lyn was also unchanged. Since the number of FcεRI on the pZeo transfectants varied between 80,000 and 150,000 (clones Z1 to Z6, Table 2), the degree of phosphorylation was found to be independent of the number of receptors under the conditions used in this study.

Mapping The Site of Lyn-FcεRI Interaction by Competition. The presence in the CHO-B12 cells of an endogenous kinase (presumably Lyn) capable of phosphorylating the receptor allowed for probing the site on Lyn which interacts with the FcεRI by a competition protocol. Cells were transfected with domains of Lyn that would potentially interact with the receptor but that were themselves catalytically inactive. The responsiveness of such transfectants to aggregation of their FcεRI was compared either to CHO-B12 or to cells co-transfected with the "empty" pZeo vector.

Catalytically Inactive Lyn Kinase. A full length, catalytically inactive Lyn B kinase was prepared by mutating Lys279 to Arg (RK Lyn). In a coupled in vitro transcription-translation reaction, the wild-type Lyn was autophosphorylated, whereas the mutant Lyn was not.

Three stable transfectants expressing substantial amounts of the mutant Lyn were isolated and assessed (clones RK 17, 21 and 26 in Table 2). The catalytically inactive Lyn was expressed largely or exclusively as a membrane anchored protein. On a per receptor basis, such stable RK Lyn-FcεRI transfectants showed 20–75% less antigen-induced phosphorylation of receptor tyrosines than cells transfected with the vector alone. Therefore, a single point mutation converted a construct that stimulated phosphorylation of tyrosines on FcεRI to one that inhibited it.

Unique Domain of Lyn Kinase. On the basis of the results from the yeast-two hybrid studies, the unique domain of Lyn A kinase was transfected into receptor-containing cells (clones C6, U7 and U8 in Table 2). The isolated unique domain was expressed largely or exclusively in a membrane-anchored form. Upon stimulation with multivalent antigen, a partial inhibition of phosphorylation of receptor tyrosines was observed. A comparison of two clones expressing increasing levels of the unique domain protein showed that increasing amounts of the competing domain led to increasing inhibition. With a weaker stimulus (IgE trimers), complete inhibition of phosphorylation of the β and γ chains was observed at early time points and at low concentrations of stimulant.

Identifying portions of the unique domain of Lyn A and Lyn B with FcεRI signal transduction inhibiting activity. On the basis of the known sequence of the unique domain of Lyn A (amino acids 1–66) and Lyn B (amino acids 1–45), peptides having at least five contiguous amino acids from these domain sequences can be produced according to peptide synthesis protocols well known in the art and tested for the ability to bind the FcεRI βc according to protocols known in the art and as described herein (e.g., the yeast two hybrid assay). The peptides which bind the FcεRI βc can then be evaluated for the ability to inhibit signal transduction through the receptor according to well known methods and as described herein (e.g., inhibition of receptor phosphorylation in a transfection assay). For example, the peptides having amino acids 1–10 (SEQ ID NO:1), 1–27 (SEQ ID NO:2) and 27–66 (SEQ ID NO:3), which are known to bind FcεRI βc can be evaluated for the ability to inhibit the signal transducing activity of the receptor by the methods herein. In addition, one or more amino acids can be deleted from these peptides or one or more amino acids can be added to these peptides and evaluated according to the teachings herein for the ability to bind FcεRI βc and inhibit its signal transducing activity.

Treatment of an allergic disorder in a human with the nucleic acid or fusion protein of the present invention. Either 1) the nucleic acid of this invention, as naked DNA or carried in a vector in a pharmaceutically acceptable carrier, or 2) the fusion protein of this invention, in a pharmaceutically acceptable carrier, can be administered intranasally or by inhalation to a human subject diagnosed with an allergic disorder, in an amount and for a time interval determined by one of skill in the art to be effective in treating the allergic disorder according to standard protocols for determining optimal dosages and treatment regimens as described herein. Clinical parameters can be monitored over time as described herein and the treatment can be continued until the allergic disorder is improved or subsides. Treatment can be resumed upon the recurrence of symptoms or other clinical indicators that an allergic disorder is being manifested.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

1. Keegan, A. D. and Paul, W. E. (1992) *Immunol. Today* 13,63–68
2. Cambier, J. C. (1995) *J. Immunol.* 155,3281–3285
3. Pribluda, V. S., Pribluda, C., and Metzger, H. (1994) *Proc. Natl. Acad. Sci. USA* 91,11246–11250
4. Yamashita, T., Mao, S.-Y., and Metzger, H. (1994) *Proc. Natl. Acad. Sci. USA* 91,11251–11255
5. Eiseman, E. and Bolen, J. B. (1992) *Nature* 355,78–80
6. Torigoe, C., Goldstein, B., Wofsy, C., and Metzger, H. (1997) *Proc. Natl. Acad. Sci. USA* 94,1372–1377
7. Jouvin, M.-H. E., Adamczewski, M., Numerof, R., Letourneur, O., Valle, A., and Kinet, J.-P. (1994) *J. Biol. Chem.* 269,5918–5925
8. Lin, S., Cicala, C., Scharenberg, A. M., and Kinet, J. P. (1996) *Cell* 85,985–995
9. Wilson, B. S., Kapp, N., Lee, R. J., Pfeiffer, J. R., Martinez, A. M., Platt, Y., Letourneur, F., and Oliver, J. M. (1995) *J. Biol. Chem.* 270,4013–4022

10. Kihara, H. and Siraganian, R. P. (1994) *J. Biol. Chem.* 269,22427–22432
11. Fields, S. and Sternglanz, R. (1994) *Trends. Genet.* 10,286–292
12. Liu, F. T., Bohn, J. W., Ferry, E. L., Yamamoto, H., Molinaro, C. A., Sherman, L. A., Klinmnan, N. R., and Katz, D. H. (1980) *J. Immunol.* 124,2728–2737
13. Bazin, H., Querinjean, P., Beckers, A., Heremans, J. F., and Dessy, F. (1974) *Immunology.* 26,713–723
14. Holowka, D. and Metzger, H. (1982) *Mol. Immunol.* 19,219–227
15. Kulczycki, A.,Jr. and Metzger, H. (1974) *J Exp. Med.* 140,1676–1695
16. McConahey, P. J. and Dixon, F. J. (1966) *Intl Arch Allergy Appl Immunol* 29,185–189
17. Taurog, J. D., Mendoza, G. R., Hook, W. A., Siraganian, R. P. and Metzger, H. (1977) *J. Immunol.* 119,1757–1761
18. Barsumian, E. L., Isersky, C., Petrino, M. G. and Siraganian, R. P. (1981) *Eur. J. Immunol.* 11,317–323
19. Summers, M. D. and Smith, G. E. (1988) *Texas Agricultural Experiment Station Bulletin No.*1555
20. Gubler, U. and Hoffman, B. J. (1983) *Gene* 25,263–269
21. Minoguchi, K., Kihara, H., Nishikata, H., Hamawy, M. M., and Siraganian, R. P. (1994) *Mol. Immunol.* 31,519–529
22. Yamanashi, Y., Fukushige, S., Semba, K., Sukegawa, J., Miyajima, N., Matsubara, K., Yamamoto, T. and Toyoshima, K. (1987) *Mol. Cell Biol.* 7,237–243
23. Yi, T. L., Bole, J. B. and Ihle, J. N. (1991) *Mol. Cell Biol.* 11,2391–2398
24. Rider, L. G., Raben, N., Miller, L. and Jelsema, C. (1994) *Gene* 138,219–222
25. Alber, G., Kent, U. M. and Metzger, H. (1992) *J. Immunol.* 149,2428–2436
26. Rivera, J., Kinet, J.-P., Kim, J., Pucillo, C. and Metzger, H. (1988) *Mol. Immunol.* 25,647–661
27. Matthyssens, G. E., Hurwitz, E., Givol, D. and Sela, M. (1975) *Mol. Cell. Biochem.* 7,119–126
28. Pribluda, V. S. and Metzger, H. (1992) *Proc. Natl. Acad. Sci. USA* 89,11446–11450
29. Bartel, P. L., Chien, C.-T., Stemglanz, R. and Fields, S. (1993) *BioTechniques* 14,920–924
30. Pleiman, C. M., Abrams, C., Gauen, L. T., Bedzyk, W., Jongstra, J., Shaw, A. S. and Cambier, J. C. (1994) *Proc. Natl. Acad. Sci. USA* 91,4268–4272
31. Timson Gauen, L. K., Kong, A. N., Samelson, L. E. and Shaw, A. S. (1992) *Mol. Cell Biol.* 12,5438–5446
32. Resh, M. D. (1993) *Biochim. Biophys. Acta* 1155, 307–322
33. Michieli, P., Li, W., Lorenzi, M. V., Miki, T., Zakut, R., Givol, D., and Pierce, J. H. (1996) *Oncogene* 12, 775–784.
34. Lewin, "Genes V" Oxford University Press Chapter 7, pp. 171–174 (1994).
35. Lewin, "Genes V" Oxford University Press Chapter 1, pp. 9–13 (1994).
36. Marsh, D. G. and P. S. Norman. Antigens that cause atopic diseases. pp. 981–1002. In: *Immunological Diseases*, Vol. II, Fourth edition. M. Samter et al., eds.
37. Toda, T. 1975. Regulation of reagin formation. *Prog. Allergy.* 19:122.
38. Grammer, L. C. Principles of immunologic management of allergic diseases due to extrinsic antigens. pp. 358–373. In: *Allergic Diseases, Diagnosis and Management*, Third edition. R. Patterson, ed.
39. Fang, K. S. Y., et al. 1988. cDNA cloning and primary structure of a white-face hornet venom allergen, antigen 5. *Proc. Natl. Acad. Sci.* 85:895–899.
40. Pastan et al. A retrovirus carrying an MDR1 cDNA confers multidrug resistance and polarized expression of P-glycoprotein in MDCK cells. *Proc. Nat. Acad. Sci.* 85:4486 (1988)
41. Miller et al. Redesign of retrovirus packaging cell lines to avoid recombination leading to helper virus production. *Mol. Cell Biol.* 6:2895 (1986).
42. Mitani et al. Transduction of human bone marrow by adenoviral vector. *Human Gene Therapy* 5:941–948 (1994).
43. Goodman et al. "Recombinant adeno-associated virus-mediated gene transfer into hematopoietic progenitor cells." *Blood* 84:1492–1500 (1994)
44. Naidini et al. "In vivo gene delivery and stable transduction of nondividing cells by a lentiviral vector." *Science* 272:263–267 (1996)
45. Agrawal et al. "Cell-cycle kinetics and VSV-G pseudotyped retrovirus mediated gene transfer in blood-derived $CD34^+$cells." *Exp. Hematol.* 24:738–747 (1996).
46. Schwarzenberger et al. "Targeted gene transfer to human hematopoietic progenitor cell lines through the c-kit receptor. " *Blood* 87:472–478 (1996).
47. Martin, E. W. (ed.) *Remington 's Pharmaceutical Sciences*, latest edition. Mack Publishing Co., Easton, Pa.
48. Crystal, R. G. 1997. Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985–1001.
49. Alvarez, R. D. and D. T. Curiel. 1997. A phase I study of recombinant adenovirus vector-mediated delivery of an anti-erbB-2 single chain (sFv) antibody gene from previously treated ovarian and extraovarian cancer patients. *Hum. Gene Ther.* 8:229–242.
50. Saveria-Campo (1985) in DNA Cloning, Vol. II, *A Practical Approach*, D. M. Glover, ed., IRL Press, Arlington, Va., pp. 213–238.
51. Botstein et al. 1979. *Gene* 8:17–24.
52. Broach et al. 1979. *Gene* 8:121–133.
53. Sprague et al. 1983. *J. Virol.* 45:773–781.
54. Schneider, J. 1987. *Embryol. Exp. Morphol.* 27:353–365.
55. Sherman et al. 1982. *Methods in Yeast Genetics*, Cold Spring Harbor Laboratory.
56. Hinnen et al. 1987. *Proc. Natl. Acad. Sci. USA* 75:1929–1933.
57. Ito et al. 1983. *J. Bact.* 153:163–168.
58. Quean et al. 1986. *Immunol. Rev.* 89:49.
59. Beggs, J. D. 1978. *Nature* 275:104–109.
60. Sambrook et al., *Molecular Cloning: A Laboratory Manual.* 2nd Ed., Cold Spring Harbor Laboratory, Cold Spring Harbor, N.Y. (1989)
61. Kardon, E. M., Acute asthma. *Emerg. Med. Clin. North Am.* 14:93–114.
62. Powell, C. V., 1993. Management of acute asthma in childhood. *Br. J. Hosp. Med.* 50:272–5.
63. Tagge, E., et al., 1996. Preproricin expressed in *Nicotiana tabacum* cells in vitro is fully processed and biologically active. *Protein Purification and Expression* 8:109–118.
64. Hogan, et al., 1986. In *"Manipulating the Mouse Embryo: A Laboratory Manual"* Cold Spring Harbor, N.Y.: Cold Spring Harbor Laboratory.
65. Kinet, J. P., et al. 1987. Isolation and characterization of cDNAs coding for the beta subunit of the high-affinity receptor for Immunoglobulin E. *Proc. Natl. Acad. Sci. USA* 85(17):6483–6487.

TABLE 1

CONSERVATIVE SUBSTITUTIONS

| Shared properties | Amino acids which are interchangeable for each other |
|---|---|
| Neutral and hydrophobic | Alanine (Ala A); Valine (Val V); Leucine (Leu L); Isoleucine (Ile I); Proline (Pro P); Tryptophan (Trp W); Phenylalanine (Phe F); Methionine (Met M) |
| Neutral and polar | Glycine (Gly G); Serine (Ser S); Threonine (Thr T); Tyrosine (Tyr Y); Cysteine (Cys C); Glutamine (Gln Q); Asparagine (Asn N) |
| Basic | Lysine (Lys K); Arginine (Arg R); Histidine (His H) |
| Acidic | Aspartic Acid (Asp D); Glutamic Acid (Glu E) |

TABLE 2

CHO TRANSFECTANTS

| Name | Clone | Insert | FcεRI × $10^{-5}$ | Lyn per FcεRI[c] | Lyn (Inact.) per Lyn (End.) |
|---|---|---|---|---|---|
| CHO—B12[a] | B12 | NA[b] | 1.7 | 2.5 | NA |
| Lyn/B12 | A6 | Lyn B | 1.0 | 1.0 | NA |
| Lyn/B12 | A9 | Lyn B | 0.7 | 9.3 | NA |
| Lyn/B12 | A11 | Lyn B | 1.3 | 66 | NA |
| Lyn/B12 | D1 | Lyn B | 1.3 | 34 | NA |
| Lyn/B12 | D7 | Lyn B | 1.3 | 3.2 | NA |
| Lyn/B12 | D8 | Lyn B | 1.3 | 0.94 | NA |
| RK Lyn/B12 | RK17 | Inact.Lyn B | 1.9 | 7.4 | 6.0[d] |
| RK Lyn/B12 | RK21 | Inact.Lyn B | 1.8 | 4.6 | 4.2 |
| RK Lyn/B12 | RK26 | Inact.Lyn B | 1.4 | 24 | 12 |
| Lyn unique/B12 | C6 | Unique Lyn A | 1.2 | 5.9 | 5.0 |
| Lyn unique/B12 | U7 | Unique Lyn A | 1.0 | 0.83 | 0.42 |
| Lyn unique/B12 | U8 | Unique Lyn A | 1.7 | 1.9 | 0.76 |
| pZeo/B12 | Z1 | None | 0.8 | 5.2 | NA |
| pZeo/B12 | Z2 | None | 0.8 | 6.6 | NA |
| pZeo/B12 | Z3 | None | 1.0 | 5.0 | NA |
| pZeo/B12 | Z4 | None | 0.8 | 6.8 | NA |
| pZeo/B12 | Z5 | None | 1.5 | 2.8 | NA |
| pZeo/B12 | Z6 | None | 1.0 | 6.6 | NA |

[a]A stable CHO FcεRI transfectant (CHO—B12) was generated by electroporation of FcεRI subunits (α, β, γ). Stable double transfectants, likewise generated electroporation, were prepared by transfecting various Lyn constructs into CHO—B12 cells and selection with zeocin. Control cells, doubly transfected with FcεRI and empty pZeo vectors, were prepared by the same protocol.
[b]NA, not applicable
[c]The values shown in this column are strictly relative and were determined as follows. For each transfectant, the normalized densitometric readings of the total Lyn in a fixed number of cell equivalents was divided by the number of FcεRI per cell × $10^{-3}$. For example, for the first item in this column the corrected densitometric reading was 430.6. The latter divided by 170 (FcεRI per cell × $10^{-3}$) equals 2.5. The quantitation of Lyn was done two to eight times for each transfectant; the enumeration of the FcεRI was done in duplicate.
[d]The amount of endogenous hamster Lyn (Lyn (End.)) and transfected inactive Lyn (Lyn(Inact.)) expressed per cell was determined by Western blotting of SDS lysates with anti-(human) Lyn. The values shown represent the average of two to eight separate determinations.

What is claimed is:

1. An isolated nucleic acid selected from the group consisting of:
   a) a nucleic acid encoding the amino acid sequence consisting of amino acids 1–66 of the human tyrosine kinase, Lyn A (SEQ ID NO:1);
   b) a nucleic acid encoding the amino acid sequence consisting of amino acids 1–10 of the human tyrosine kinase, Lyn A (SEQ ID NO:3); and
   c) a nucleic acid encoding the amino acid sequence consisting of amino acids 27–66 of the human tyrosine kinase, Lyn A (SEQ ID NO:5).

2. A vector comprising the nucleic acid of claim 1.

3. The nucleic acid of claim 1 in a pharmaceutically acceptable carrier.

4. A cell comprising the vector of claim 2.

5. An isolated nucleic acid encoding the amino acid sequence of amino acids 1–45 of the human tyrosine kinase, Lyn B (SEQ ID NO:2).

6. A vector comprising the nucleic acid of claim 5.

7. The nucleic acid of claim 5 in a pharmaceutically acceptable carrier.

8. A cell comprising the vector of claim 6.

9. An isolated nucleic acid encoding the amino acid sequence of a fusion protein, comprising i) a nucleic acid encoding a ligand which binds to and is internalized by cells which express a high affinity receptor for IgE on the surface and ii) a nucleic acid selected from the group consisting of:
   a) a nucleic acid encoding the amino acid sequence of amino acids 1–66 of the human tyrosine kinase, Lyn A (SEQ ID NO:1);
   b) a nucleic acid encoding the amino acid sequence of amino acids 1–10 of the human tyrosine kinase, Lyn A (SEQ ID NO:3);
   c) a nucleic acid encoding the amino acid sequence of amino acids 1–27 of the human tyrosine kinase, Lyn A (SEQ ID NO:4);
   d) a nucleic acid encoding the amino acid sequence of amino acids 27–66 of the human tyrosine kinase, Lyn A (SEQ ID NO:5); and
   e) a nucleic acid encoding a peptide comprising any five or more contiguous amino acids of the amino acid sequence of amino acids 1–66 of the human tyrosine kinase, Lyn A, wherein the peptide has the same IgE (FcεRI) receptor binding activity as the amino acid sequence encoded by the nucleic acid sequence as set forth in (a), (b), (c) or (d).

10. A vector comprising the nucleic acid of claim 9.

11. The nucleic acid of claim 9 in a pharmaceutical carrier.

12. The nucleic acid of claim 9, wherein the ligand is selected from the group consisting of IgE and c-Kit.

13. A cell comprising the vector of claim 10.

14. An isolated nucleic acid encoding the amino acid sequence of a fusion protein, comprising i) a nucleic acid encoding a ligand which binds to and is internalized by cells which express a high affinity receptor for IgE on the surface and ii) a nucleic acid selected from the group consisting of:
   a) a nucleic acid encoding the amino acid sequence of amino acids 1–45 of the human tyrosine kinase, Lyn B (SEQ ID NO:2); and
   b) a nucleic acid encoding a peptide comprising any five or more contiguous amino acids of amino acids 1–45 of the human tyrosine kinase, Lyn B (SEQ ID NO:2), wherein the peptide has the same IgE (FcεRI) receptor binding activity as the amino acid sequence encoded by the nucleic acid sequence as set forth in (a).

15. A vector comprising the nucleic acid of claim 14.

16. The nucleic acid of claim 14 in a pharmaceutically acceptable carrier.

17. The nucleic acid of claim 14, wherein the ligand is selected from the group consisting of IgE and c-Kit.

18. A cell comprising the vector of claim 15.

* * * * *